US008382656B1

(12) United States Patent
Brown

(10) Patent No.: US 8,382,656 B1
(45) Date of Patent: Feb. 26, 2013

(54) APPARATUS AND METHOD FOR FACILITATING MALE ORGASM

(76) Inventor: Ronald Allen Brown, Kailua-Kona, HI (US)

(*) Notice: Subject to any disclaimer, the term of this patent is extended or adjusted under 35 U.S.C. 154(b) by 0 days.

(21) Appl. No.: 13/493,374

(22) Filed: Jun. 11, 2012

Related U.S. Application Data

(63) Continuation of application No. PCT/US2011/050892, filed on Sep. 8, 2011.

(51) Int. Cl.
*A61F 5/00* (2006.01)
(52) U.S. Cl. .......................................................... 600/38
(58) Field of Classification Search ................ 600/38–41
See application file for complete search history.

(56) References Cited

U.S. PATENT DOCUMENTS

| | | | |
|---|---|---|---|
| 3,631,853 A | 1/1972 | Burdette, Jr. | |
| 5,234,401 A | 8/1993 | Yamanaka | |
| 5,458,559 A * | 10/1995 | Gauntlett | 600/38 |
| 5,647,837 A | 7/1997 | McCarty | |
| 5,707,341 A | 1/1998 | Mathewuse | |
| 5,836,864 A | 11/1998 | Clark, Jr. | |
| 6,036,635 A | 3/2000 | Altshuler | |
| 6,248,059 B1 | 6/2001 | Gamper et al. | |
| 6,398,720 B1 | 6/2002 | Dabal | |
| 6,458,073 B1 * | 10/2002 | Bonthuys | 600/38 |
| 6,905,459 B2 | 6/2005 | Humphries | |
| 7,261,685 B2 | 8/2007 | Wu | |
| 7,572,220 B2 * | 8/2009 | Nan | 600/38 |
| 2003/0136415 A1 | 7/2003 | Lanton | |
| 2005/0033113 A1 | 2/2005 | Bonthuys | |
| 2005/0119521 A1 | 6/2005 | Pitcher | |
| 2006/0235266 A1 | 10/2006 | Nan | |
| 2008/0269650 A1 | 10/2008 | Nan | |

FOREIGN PATENT DOCUMENTS

WO 96-07375 A1 3/1996

* cited by examiner

*Primary Examiner* — John Lacyk
(74) *Attorney, Agent, or Firm* — Seth M. Reiss, AAL, ALLLC; Seth M. Reiss

(57) ABSTRACT

A male masturbation device and method for using same facilitates orgasm without the necessity of the subject achieving an erection. The novel device comprises a housing (14) and accumulator means (12). The accumulator means maintains a consistent modest vacuum within the housing notwithstanding sliding of the penis within the housing. The accumulator means can be integrated with the housing or detached from but in fluid communication with the housing. The device may be used with or without a partner and its use may be augmented by sensory stimulation contrivances. The novel device and method offers the health and recreational benefits of orgasm, and facilitates semen collection, for individuals suffering ED, without resort to drugs or vacuum erection devices. The novel device takes advantage of the fact that an erection is not required for orgasm, however, users may experience an erection prior to ejaculation.

29 Claims, 10 Drawing Sheets

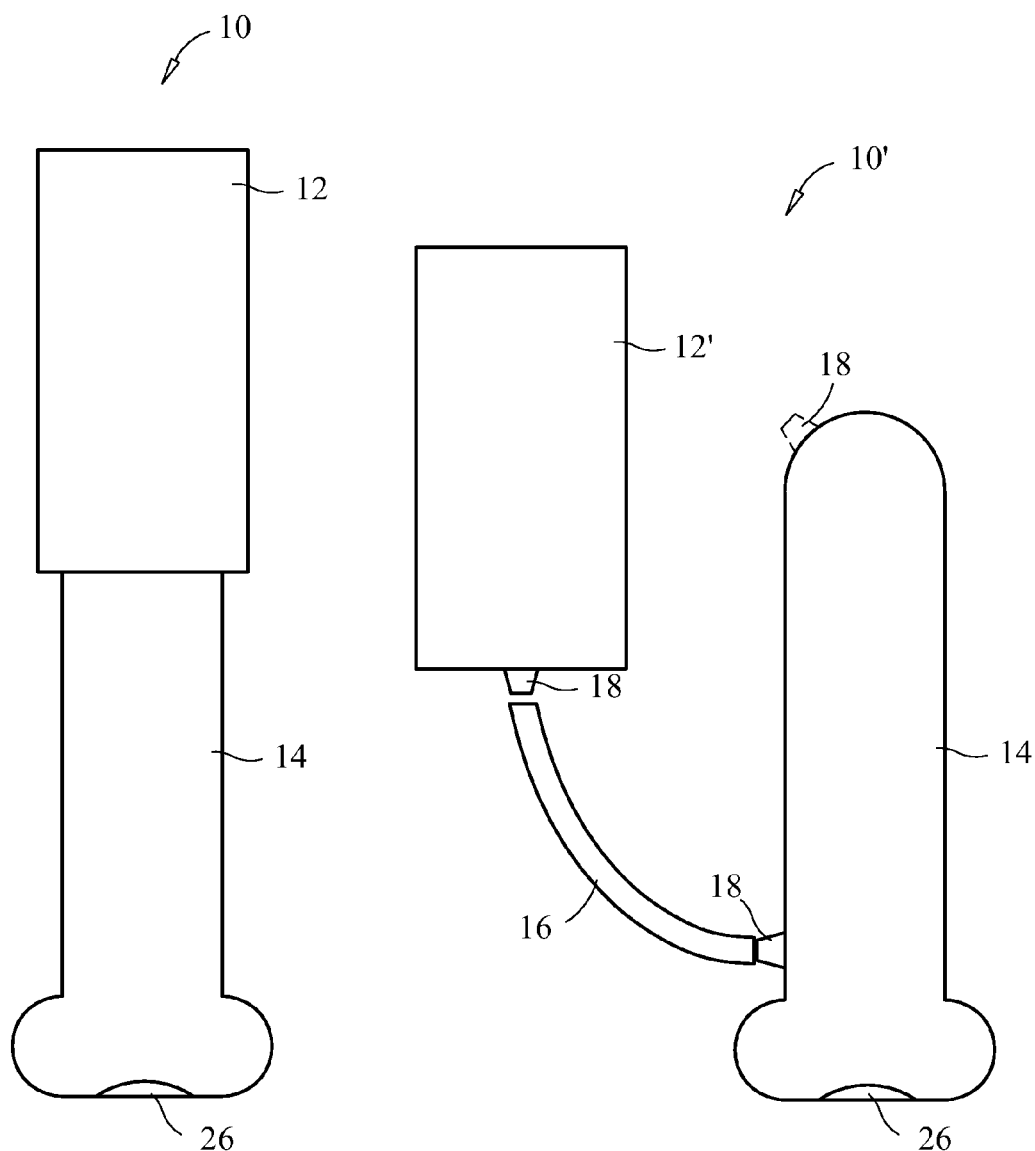

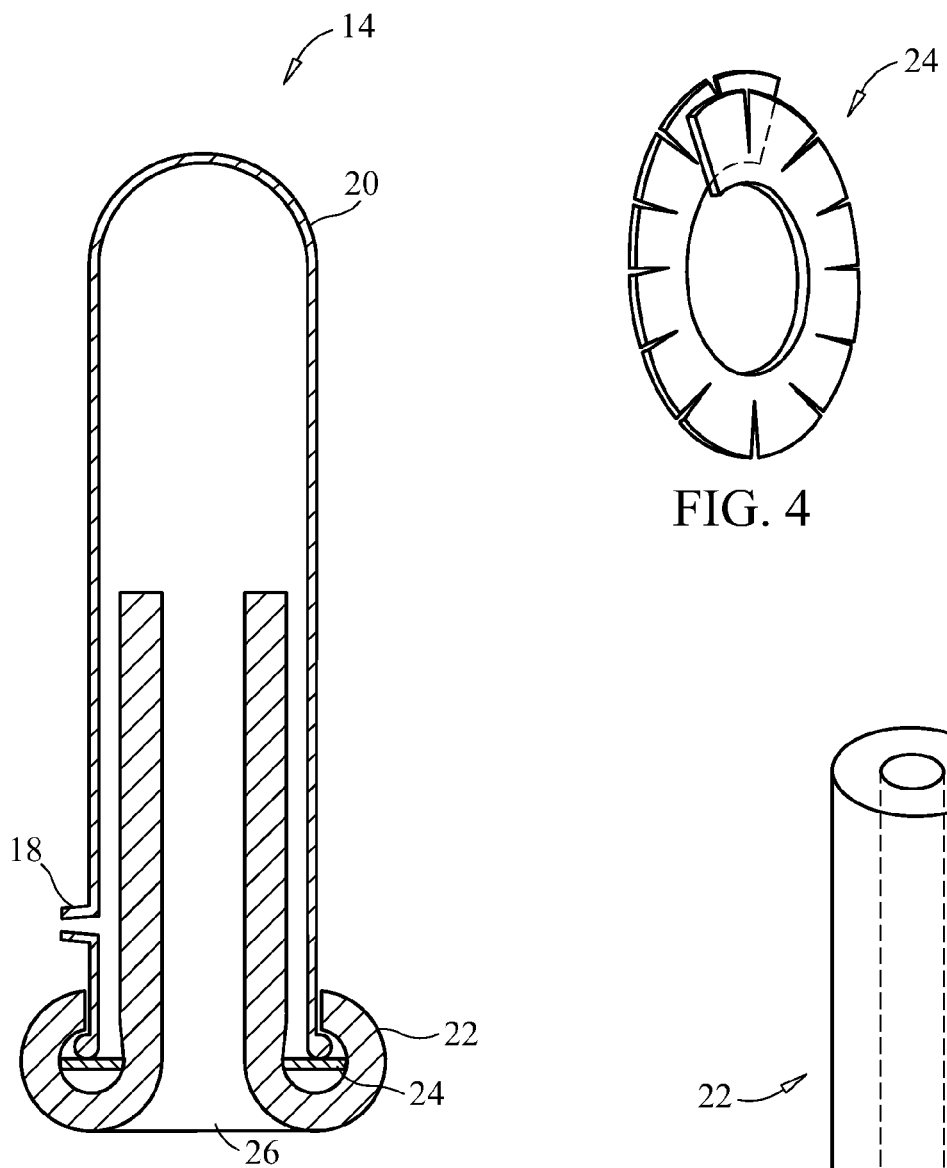
FIG. 3
FIG. 4
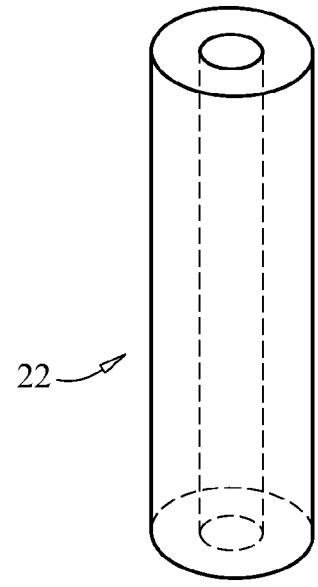
FIG. 5

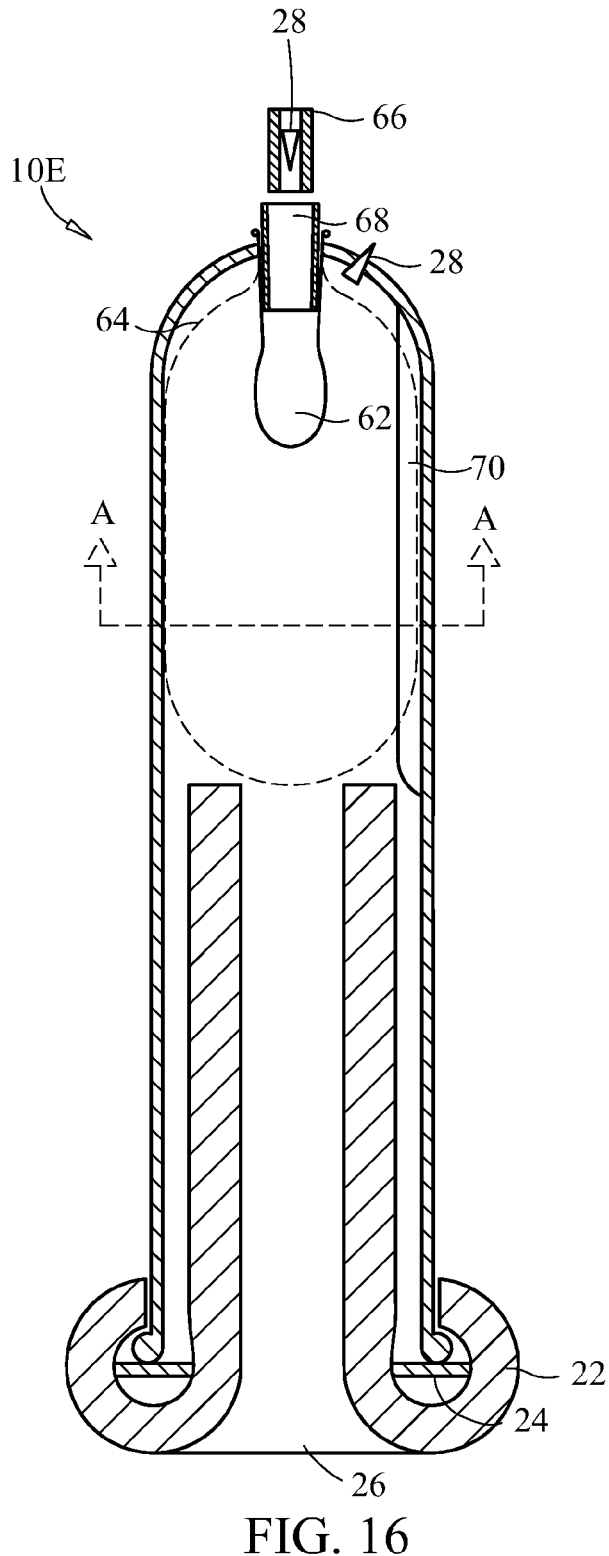
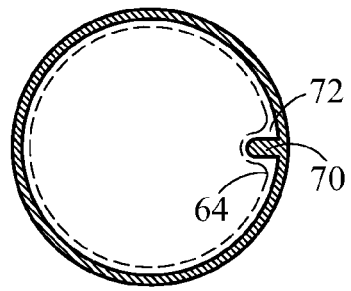
FIG. 16
FIG. 16A

APPARATUS AND METHOD FOR FACILITATING MALE ORGASM

CROSS-REFERENCE

This patent application is a continuation and claims the benefit of Patent Cooperation Treaty International Application No. PCT/US2011/050892 filed 8 Sep. 2011, which application is incorporated in its entirety by this reference.

BACKGROUND OF THE INVENTION

1. Technical Field

This invention comprises a device and method for facilitating male orgasm. More specifically, this invention comprises a device that males, and couples, can use to facilitate male masturbation and orgasm without the necessity of first achieving an erection, and a method of using the same.

2. Background Art

To facilitate understanding of this invention, two points must be emphasized at the outset. Firstly, this invention is not a VED (vacuum erection device), whose function, result, and operating pressures are substantially at odds with the present invention. VEDs subject the penis to a substantial vacuum in the range of 26-31 cm Hg for a period of time during which the penis becomes engorged with blood while the user may experience mild discomfort. While a VED is under a 26-31 cm Hg vacuum, partial withdrawal of the penis, or sliding the device, is impeded because, in accordance with Boyle's Law, partial withdrawal of the penis would significantly increase the vacuum pressure, beyond a safe level, causing risk of pain and injury to the penis. Use of a VED generally does not provide a pleasant sensation which might facilitate an orgasm. The relatively constant modest vacuum of about 5 cm Hg which is maintained by the present invention is insufficient to produce an erection, but instead facilitates masturbation and orgasm with a flaccid penis.

VEDs of various designs are widely known, and a number have been patented. VEDs are currently marketed in the United States in a price range from $10 to $550, the $550 VED being recognized by the U.S. Food and Drug Administration for inclusion in the government Medicare program as an approved device to treat erectile dysfunction (ED), while the $10 VED provides the same result, in the same way, in the same amount of time. VEDs are highly effective at producing an erect penis, which the subject may then proceed to use as he will. VEDs are not intended to produce an orgasm.

The second point to be understood is that an erection is not required for male orgasm, a fact which has been known in certain academic circles since the 1960s, but the myth persists that an erection must precede orgasm. June M. Reinisch, Ph.D., has recorded a 15-minute video clip in which she explains the physiology of male orgasm and why an erection is not a necessary part of the orgasm process. Dr. Reinisch's video, and a transcription of the audio portion thereof, may be accessed at http://loveandhealth.worldgroups.com/Article.cfm?Article=157&SubTopic=18&Topic=2

Excerpts from the transcript of the audio portion of Dr. Reinisch's presentation are reproduced below.

Myth: Erections Are Necessary for Orgasm

June M. Reinisch, Ph.D.

The myth that we're going to bust this month is one that you probably don't even know you have, but I think it has probably affected, or will affect, if it hasn't, your sex life sometime in your life—and not just you men who are listening to this but your partners' lives. And I think it's an important one that we address, so we're going to address it this month. The myth is that a man must have an erection in order to have an orgasm and an ejaculation. But the orgasm part I think is the most important because that's the pleasure part. And it's a myth that not just men have out there who are ordinary guys, but it's a myth that physicians actually carry around with them, and a lot of scientists don't know about. We sexologists, of course, know it's not true . . . .

The fact is that men can have orgasms even if they have no erections whatsoever. An erection is not necessary for orgasm or, in fact, ejaculation, because they're all separate events. They just happen to happen together, but they're not inseparable—they're not the same thing. Very simply put, this means that even if a man cannot produce any erection at all or can only attain or maintain a partial erection, with appropriate manual or oral stimulation he can experience a complete and fully satisfying orgasm and an ejaculation . . . .

Now the revelation of the independence of arousal and erection from ejaculation and orgasm provided what might be considered the most important insight leading to the development of modern sex therapy. The independent nature of these phases of sexual response should have made front page news. Here's the headlines that I see we could have had. We should have had headlines like—of course in America we wouldn't have them, knowing how uptight we are and how puritan we are—but I can see headlines like "Orgasm Freed from Servitude of Erection," or how about "Men's Pleasure Liberated from the Demands of Erection" but as you know, we didn't get any of that. In fact, hardly any physicians even found out about it. Because four decades later, after the original medical report, most people, and that includes physicians, are still unaware that with appropriate stimulation of the man's penis, he can experience a full orgasm even when he has little or no erection . . . .

Now the anatomical basis for the independence of erection, ejaculation, and orgasm has been known and understood in some quarters long before it was applied to clinical practice . . . .

The first part of these orgasm phase events is called emission. That's when semen is collected from the testes and other internal organs . . . .

The second event is ejaculation. And that occurs almost immediately after emission and involves strong spasmodic muscle contractions which propel the semen through the urethra and out the end of the penis, in spurts. Then the third part, of course, is orgasm, that accompanies the ejaculation . . . .

So—I guess the moral of this myth-busting session is that if you find yourself in a situation when an erection is not forthcoming because maybe you've drunk a little bit too much or you're sick or there's something else going on, or you're taking a medication that at this point in your life is interfering with your erections, now you know not to give up. Don't give up the ship! This is a time to say to your partner, or even to yourself if you're masturbating, that the pleasure is still there and that if you keep at it and you do the things that make you feel good, then you will have an orgasm, and of course there are other ways to satisfy your partner. So keep at it, and know that your body wants to give you pleasure and that an erection is not necessary in order to have pleasure.

According to the Cleveland Clinic, http://www.clevelandclinicmeded.com/medicalpubs/diseasemanagement/endocrinology/ere ctile-dysfunction/#cesec7, ED affects 52% of males over age 40, and the prevalence and severity of ED at all ages is increasing, as a side effect of growing health problems, notably obesity and diabetes.

The initial primary beneficiaries of this invention will necessarily be adult males in the so-called "more developed countries", simply because they can afford it, and are likely to become aware of it. From now through 2050, according to U.N. projections, the total population of the more developed countries will remain flat (at 1.25 billion), but is rapidly aging. Today, 62% of the 480 million adult males in the more developed countries are over age 40, and those over age 40 will increase to 68% by 2050. Aging is a primary factor in the onset of ED. See the 2008 World Population Data Sheet by the Population Reference Bureau, available at http://www.scribd.com/doc/6502276/2008-World-Population-Presentation.

There exists a variety of pharmaceuticals and apparatus designed to facilitate an erection among those experiencing ED. Pharmaceuticals used to facilitate erections among males have significant side effects and are contraindicated for individuals with certain medical conditions. The apparatus that facilitates male erections can be expensive, cumbersome, difficult to use and may be painful or irritating to the user.

Among the apparatus most commonly employed to facilitate erection in men experiencing ED are vacuum erection devices. VEDs function by employing a vacuum to draw blood into the penis, engorging the tumescent tissues of the penis and facilitating an erection. Numerous prior art patents and published literature describe a wide variety of VED erection aids and a variety is available commercially. The purpose and function of all VEDs is assisting the male organ to achieve an erection.

VEDs require a minimum vacuum of approximately 28 cm Hg to promote an erection in a male experiencing ED. A vacuum of this magnitude makes sliding of the VED along the shaft of the penis impossible. Any attempt to slide a penis being held within a VED under a vacuum of 28 cm Hg or more would be painful and would cause injury to the male organ. For the same reason, it is necessary to release the vacuum in the VED in order to safely and painlessly withdraw the penis from a VED. These characteristics make VEDs unsuitable for masturbation and facilitating orgasm.

Accordingly, there would appear to be a need for a device and method to facilitate masturbation and orgasm in males experiencing ED, without the need to first create an erection by employing pharmaceuticals or awkward and uncomfortable mechanical devices.

An erection is not a prerequisite to male masturbation and orgasm. Yet available manual masturbation aids and sex toys do not function to facilitate male masturbation and orgasm with a flaccid penis. There would appear to be the need for a device that facilitates manual masturbation, orgasm and ejaculation in the absence of an erection.

Individuals with more severe cases of ED, and those of advanced age, typically require a higher level of stimulation in order to achieve orgasm. Prostate massage is one method which can be helpful in promoting orgasm in these individuals and a number of prostate massage devices are available commercially. These devices typically are made of rubber or silicone and may include a vibrator. One end of the device is inserted anally to contact the prostate while an external portion contacts the perineum. Because currently available manual masturbation devices do not work with a flaccid penis, there is a need for a device that can be used in conjunction with prostate massage devices to facilitate masturbation and orgasm in individuals with advanced ED who are not able to, or are unlikely to, achieve an erection without resorting to VEDs or pharmaceutical agents.

BRIEF SUMMARY OF INVENTION

These and other objects are obtained in the novel device of the subject invention, a male masturbation device that facilitates masturbation, orgasm and ejaculation without the necessity of the subject achieving an erection, and a novel method for using this device. The novel device and method offers the health and recreational benefits of masturbation and orgasm, and facilitates semen collection following ejaculation, for individuals suffering ED, without the individual having to resort to drugs, or mechanical erection-facilitating devices.

The novel device of the subject invention comprises a housing and an accumulator means. The accumulator means is either integrated with the housing of the masturbation device or is detached and in fluid communication with the housing.

The housing of the masturbation device may further comprise a resilient masturbation sleeve to receive the penis, a variable aperture at the proximal end of the housing capable of forming a hermetic seal around a lubricated penis and maintaining the seal during use of the device, a rigid or, in some embodiments depressible, enclosure that withstands a vacuum pressure of at least 11 cm Hg and, in some embodiments, a check valve which allows compressed air within the housing of the device to escape.

According to one embodiment, a remote accumulator means maintains a modest vacuum, preferably within the range of 4 to 7 cm Hg, within the masturbation device housing. This modest vacuum is used to draw the penis into the masturbation device and also to maintain the penis within the masturbation device when the device is manipulated to stimulate the penis and promote orgasm.

According to alternative embodiments of the masturbation device of the present invention, the device housing is formed with a flexible surface or surface portion which, together with other aspects of the device housing, serves as an integrated accumulator means. When the flexible surface of the device housing is depressed and released, a partial vacuum is created, once again preferably within the range of 4 to 7 cm Hg, serving to draw the penis into the device and to maintain the penis within the device during use. The integrated accumulator means of other preferred embodiments employ an inflatable element.

The method of the subject invention involves placing the glans of a lubricated penis into the opening of the device housing, followed by using either the remote or integrated accumulator means to draw the penis into the device, and then manipulating the penis by drawing the device housing back and forth along the shaft of the penis, or otherwise moving the penis relative to the device housing, partially withdrawing and reinserting the penis within the housing, to stimulate the penis and facilitate orgasm and ejaculation.

The accumulator means serves to maintain a modest vacuum within the device housing at the preferred range of 4 to 7 cm Hg during sliding of the penis. This vacuum is by itself insufficient to promote an erection in the typical male suffering ED. However, the user may experience a partial or full erection for other reasons as, for example, tactile and other stimulation.

The variable aperture serves to maintain a hermetic seal around the penis during manipulation and sliding, and also can accommodate tumescence of the penis should stimulation cause the penis to become partially or fully erect.

The housing can take on a variety of forms and shapes and may be constructed from a variety of materials, many of which are known in the sex-device industry. The housing may be formed to simulate a human orifice, for example, making the device more attractive and erotic to the user.

The device housing may be adapted to be held stationary by, for example, pillows, furniture, or other mount of some type, while the user moves his body back and forth relative to the restrained device housing in order to insert and withdraw the penis within the housing.

The masturbation device of the present invention includes embodiments allowing its use with a sexual partner. Some embodiments of the housing may be held between a partner's legs, possibly contacting a partner's clitoris, and may further include housings designed to be inserted into a partner's bodily orifice, and may incorporate appendages, as for example a bullet vibrator, to contact and stimulate a partner's clitoris, and may further incorporate a harness or other means to secure it in place. Such insertable embodiments lend themselves to be connected by tubing to a remote accumulator means. Alternatively, a bulb appendage so placed as to be squeezed between the partners' pubic bones (and clitoris) can function to charge, and re-charge, the device's integral accumulator as needed. Such bulb appendage may alternatively be disposed at the end of a length of flexible tubing, to be operated by either of the partners.

A further preferred embodiment of the subject invention combines a masturbation device, suitable for use with a flaccid penis, and a prostate massage apparatus.

The device of the present invention facilitates masturbation and orgasm in males irrespective of whether the male achieves a partial or complete erection. It is simple in its construction and can be fabricated cheaply from a variety of known and available components, rendering it easily accessible to individuals who experience ED and who wish to avoid the expense, delay, and side effects of mechanical or pharmaceutical erection aids.

BRIEF DESCRIPTION OF THE DRAWINGS

FIG. 1 is a schematic drawing illustrating a male masturbation device 10 of the subject invention with accumulator means integrally disposed at its distal end allowing use with a flaccid penis.

FIG. 2 is a schematic drawing of an alternative embodiment 10' of the male masturbation device of the subject invention with a remote accumulator means in fluid communication therewith allowing use with a flaccid penis.

FIG. 3 schematically illustrates a longitudinal cross-section side view of a typical construction of the male masturbation device 10' of FIG. 2.

FIG. 4 is a perspective view of a component of a variable aperture means employed at the proximal end of the male masturbation device, the assembled placement of which is shown in FIG. 3.

FIG. 5 is an isometric view of the resilient masturbation sleeve employed in the masturbation device as shown in FIGS. 3, 7, 10, 15, 16 and 17.

FIG. 16 schematically illustrates masturbation device embodiment 10E showing details of the integrated accumulator means employed in this embodiment.

FIG. 16A is a cross-sectional view taken along line A-A of FIG. 16.

PARTS LIST

Figures 6, 6A:
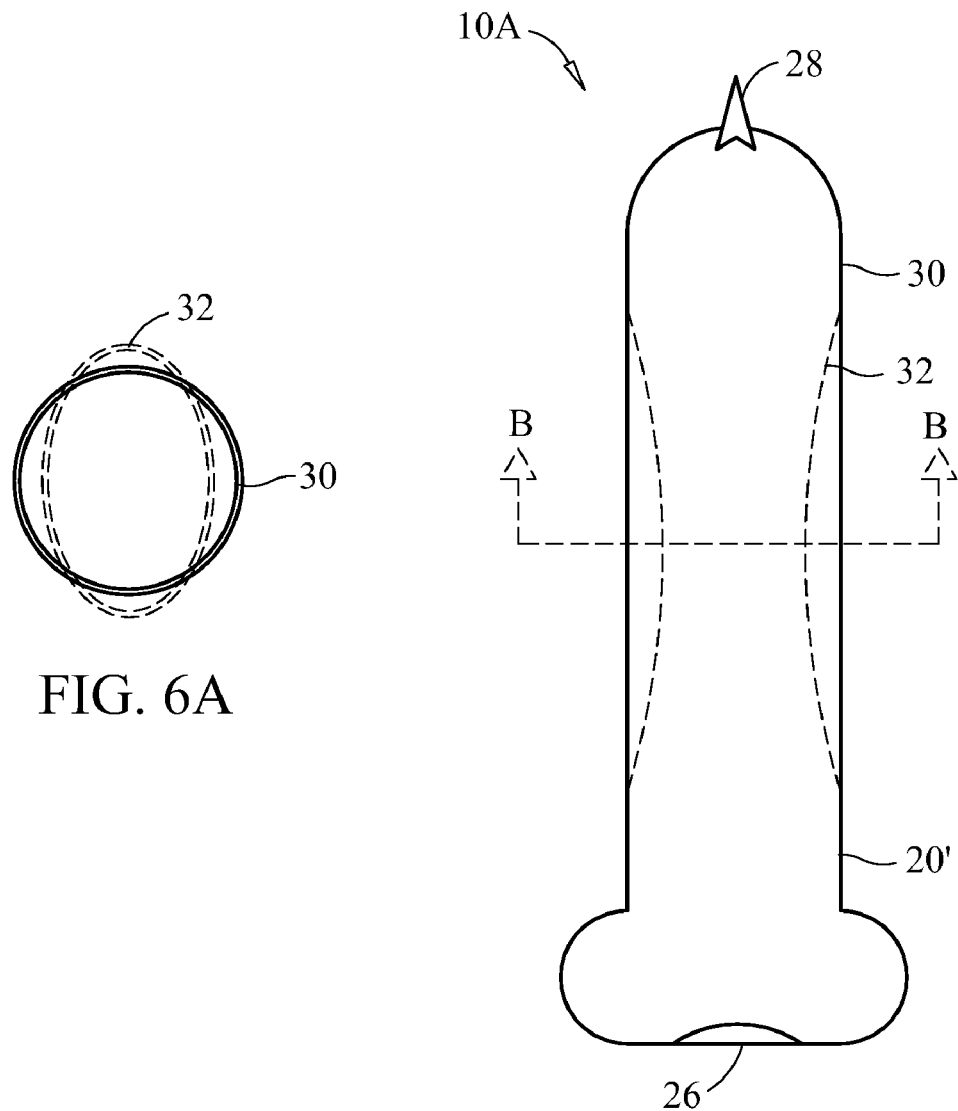
FIG. 6 schematically illustrates a masturbation device 10A with squeezable enclosure and check valve that functions in the manner of an integrated accumulator means.
FIG. 6A is a cross-sectional view taken at Line B-B of FIG. 6.

| 10 | schematic masturbation device | (with integral accumulator - FIG. 1) |
|---|---|---|
| 10' | schematic masturbation device | (with remote accumulator - FIG. 2) |
| 10A | first alternative device embodiment | (with squeezable enclosure - FIG. 6, 6A) |
| 10A' | second alternative device embodiment | (10A adapted for insertion - FIG. 6B) |
| 10B | third alternative device embodiment | (with membrane accumulator - FIG. 7) |
| 10C | fourth alternative device embodiment | (with fantasy sleeve - FIGS. 8, 9, 10) |
| 10D | fifth alternative device embodiment | (with prostate massage - FIGS. 13, 14, 15) |

-continued

| | | |
|---|---|---|
| 10E | sixth alternative device embodiment | (with balloon accumulator - FIGS. 16, 16A) |
| 10E' | seventh alternative device embodiment | (10E adapted for insertion - FIGS. 17, 17A) |
| 12 | schematic integrated accumulator means | (FIG. 1) |
| 12' | schematic remote accumulator means | (FIG. 2) |
| 14 | housing | (a device minus accumulator - FIGS. 1, 2, 3) |
| 16 | flexible tube | (FIGS. 2, 6B, 7, 17) |
| 18 | nipple | (FIGS. 2, 3, 7) |
| 20 | enclosure | (rigid enclosure - FIG. 3) |
| 20' | first alternative enclosure | (depressible enclosure - FIG. 6, 6B) |
| 20" | second alternative enclosure | (FIG. 7) |
| 20''' | third alternative enclosure | (FIGS. 8, 9, 10) |
| 22 | resilient masturbation sleeve | (FIGS. 3, 5, 7, 10, 15, 16, 17) |
| 24 | variable aperture component | (FIGS. 3, 4, 7, 10, 15, 16, 17) |
| 26 | central opening | (FIGS. 1, 2, 3, 6, 6B, 7, 8, 9, 10, 15, 16, 17) |
| 28 | check valve | (FIGS. 6, 6B, 7, 8, 9, 10, 16, 17) |
| 30 | squeezable enclosure native state | (FIGS. 6, 6A, 6B) |
| 32 | squeezable enclosure depressed state | (FIGS. 6, 6A, 6B) |
| 34 | flexible membrane native state | (FIG. 7) |
| 34' | flexible membrane depressed state | (FIG. 7) |
| 36 | enclosure cutaway section | (FIG. 8) |
| 38 | depressible tubular gripper | (FIGS. 9, 10) |
| 40 | enclosure gripper native state | (FIG. 10) |
| 40' | enclosure gripper depressed state | (FIG. 10) |
| 42a | elastic masturbation sleeve | (FIG. 11) |
| 42b | alternative elastic masturbation sleeve | (FIG. 12) |
| 44 | piston | (FIG. 15) |
| 46 | piston rod | (FIGS. 13, 14, 15) |
| 48 | ball-joint connection pivot | (FIGS. 13, 14) |
| 50 | optional handle | (FIG. 13) |
| 52 | adjustable-length extension rod | (FIG. 13) |
| 54 | stationary mount | (FIG. 13) |
| 56 | prostate massage apparatus | (FIG. 14) |
| 58 | prostate massage extension rod | (FIG. 14) |
| 60 | glans | (FIG. 14) |
| 62 | inflatable element native state | (FIGS. 16, 17) |
| 64 | inflatable element inflated state | (FIGS. 16, 17) |
| 66 | resilient inflation tube | (FIGS. 16, 17) |
| 68 | tapered breather tube | (FIGS. 16, 17) |
| 70 | internal rib | (FIGS. 16, 16A, 17, 17A) |
| 72 | air path | (FIGS. 16A, 17A) |
| 74 | vacuum source | (FIG. 6B) |
| 76 | breather nozzle | (FIG. 17) |

DETAILED DESCRIPTION OF THE PREFERRED EMBODIMENTS

The detailed description set forth below in connection with the appended drawings is intended as a description of presently-preferred embodiments of the invention and is not intended to represent the only forms in which the present invention may be constructed or utilized. The description sets forth the functions and the sequence of steps for using the invention in connection with the illustrated embodiments. However, it is to be understood that the same or equivalent functions and sequences may be accomplished by different embodiments that are also intended to be encompassed within the spirit and scope of the invention.

Schematically depicted in FIG. 1 is a first embodiment 10 of the masturbation device of the subject invention with an integrated accumulator means 12. Accumulator means 12 is disposed in direct fluid communication with masturbation device housing 14. A central opening 26 is formed within the proximal end of housing 14.

Accumulator means 12 is broadly defined as a system for maintaining a quantity of gas (air) within an enclosure at a relatively constant pressure that is less than the ambient atmospheric pressure, by changing the effective interior volume of said enclosure as a penis is repetitively inserted into and partially withdrawn from said enclosure. Accumulator means 12 can take on many configurations and forms and would be expected to employ conventional components, such as bellows, springs, pistons, siphon, cylinders, balloons, squeezable bulbs, inflatable elements, squeezable cylinders, valves, check valves, or diaphragms. Depending upon the particular embodiment, accumulators employed with the present invention are charged (initial pressure established) either prior to use of the device (pre-charged), or are charged simultaneously with initial insertion of a flaccid penis.

FIG. 2 schematically illustrates an alternative embodiment 10' of the masturbation device of the present invention with an accumulator means 12' detached from housing 14, but in fluid communication with housing 14 through a flexible tube 16. Flexible tube 16 connects to remote accumulator means 12' and housing 14 through nipples 18. Although two nipples 18 are shown projecting from housing 14 in FIG. 2, this is shown to indicate alternative positions for locating nipple 18, only one nipple 18 being necessary for any given device 10'. Nipple 18 can be located at other places on housing 14. Remote accumulator means 12' allows significant changes in the volume of air within a device (such as occurs when a penis enters masturbation device housing 14 of the present invention) while minimizing pressure changes of the air.

FIG. 3 schematically illustrates a typical construction of housing 14 of masturbation device 10', schematically shown in FIG. 2, in longitudinal cross-section. Housing 14 is comprised of a rigid enclosure 20 having an open end and a closed end, a resilient masturbation sleeve 22, and a variable aperture component 24. Enclosure 20 may be fabricated from thin-walled material, such as plastic, capable of withstanding a pressure differential of at least 11 cm Hg.

FIG. 3 also depicts one type of housing 14 that may be employed in mountable or insertable versions of the present invention which may be used with a partner. Nipple 18 disposed in the wall of enclosure 20 may be connected by tubing to a remote accumulator means as depicted in FIG. 2.

Resilient masturbation sleeve 22, shown in FIG. 3 and shown by itself in FIG. 5, is made of a flexible, resilient material having a soft inner surface suitable for being in rubbing contact with the soft tissues of the dermis of the penis.

Referring again to FIG. 3, variable aperture component 24 is installed at the open, proximal end of enclosure 20. Resilient masturbation sleeve 22 is inserted through variable aperture component 24 and into the open, proximal end of enclosure 20. The proximal end of sleeve 22 is then folded back over the proximal end of enclosure 20, thereby pneumatically sealing sleeve 22 to enclosure 20 while at the same time securing variable aperture component 24 in position and creating a central opening 26.

According to the construction of device housing 14 shown in FIG. 3, the outside diameter of variable aperture component 24, a preferred embodiment of which is shown in FIG. 4, is slightly larger than the outside diameter of the proximal end of enclosure 20. The elasticity of masturbation sleeve 22, when folded back on itself over the proximal end of enclosure 20, exerts an inward radial force on the outer circumferential edge of variable aperture component 24 thereby tending to reduce the outside diameter of variable aperture component 24 to approximately match the outside diameter of the proximal end of enclosure 20, as well as reducing the inside diameter of resilient masturbation sleeve 22 such that it will create an airtight seal around a lubricated flaccid penis during stroking motion, and will allow the penis to increase in diameter during use without creating undue friction.

Referring to FIG. 4, the variable aperture component 24 depicted may be die cut from a flat sheet of flexible plastic. The plurality of partial radial cuts as shown causes the ends to overlap at the single through cut, said partial radial cuts causing the outside circumference of variable aperture component 24 to lengthen relative to the inside circumference of variable aperture component 24, resulting in the overlap, whereby inward radial force applied at the outer circumferential edge of variable aperture component 24 increases the overlap and reduces the interior diameter of said variable aperture component 24 correspondingly.

Variable aperture component 24 can be made available with different-sized inside diameters to accommodate users having larger or smaller diameter penises, although it is intended that for any particular user, a single variable aperture component 24 will have sufficient elasticity of diameter to provide a hermetic seal for a given penis in both its flaccid and erect state. Similarly, a single variable aperture component 24 would be expected to accommodate penises of more than one size, though perhaps not all sizes.

Referring to FIG. 5, resilient masturbation sleeve 22 may be constructed of simple inexpensive tube as shown, which may include a textured interior surface to increase the pleasant sensation resulting from it being slid along the shaft of the male organ, or can have a proximal end preformed to depict a bodily orifice, or to facilitate insertion of a penis.

In an alternative embodiment, not shown, sleeve 22 may additionally include at its proximal end a preformed opening of such design and consistency as to obviate the need for variable aperture component 24. In this case a fixed-diameter aperture, provided in interchangeable sizes, performs adequately.

Schematically illustrated in FIG. 6, and in cross section (taken along line B-B of FIG. 6) in FIG. 6A, is a preferred embodiment masturbation device 10A employing a depressible enclosure 20'. Depressible enclosure 20', in conjunction with a check valve 28 installed at a convenient location on enclosure 20', forms an integrated accumulator means that facilitates the full insertion and sliding of a flaccid penis within device 10A.

In its native state 30, depressible enclosure 20' is tubular having an approximately circular circumference. As shown best in FIG. 6A, the wall of enclosure 20' may be depressed, manually, locally elastically deforming the circular wall of enclosure 20' into an elliptical depressed state 32 whereby the volume of air within enclosure 20' is reduced, causing air to be initially expelled through central opening 26. With enclosure 20' so deformed, if central opening 26 of device 10A is then closed off by a lubricated glans penis, releasing the deforming force on enclosure 20' causes the volume of air within enclosure 20' to attempt to increase to its initial volume, creating a modest vacuum and drawing the lubricated (possibly flaccid) penis into central opening 26 while allowing enclosure 20' to elastically resume its native state 30. Subsequent squeezes of enclosure 20', while manually preventing device 10A from sliding off the partially inserted penis, will expel additional air through check valve 28, causing further insertion of the penis upon release of the enclosure-deforming force, until the penis is fully inserted within device 10A.

Enclosure 20' is designed and manufactured to maintain a predetermined shape and to have a predetermined rigidity, and to be of such volume that, upon the partial withdrawal of a certain volume of a penis from enclosure 20', as for example 100 cc of volume, enclosure 20' partially collapses and decreases its volume by a lesser amount, as for example 36 cc, resulting in a net increase of air volume and a corresponding decrease in the pressure to approximately 7 cm Hg of vacuum, a pressure which encourages a flaccid penis to re-enter the device, all in accordance with Boyle's Law. Enclosure 20' thus functions in the manner of an integrated accumulator means functioning to maintain the vacuum within enclosure 20' within the range of 4 to 7 cm Hg.

Once the penis is fully inserted within device 10A, the device may be further manipulated by sliding it part way off the penis, causing enclosure 20' to partially collapse into depressed state 32, while reducing its internal pressure to approximately 7 cm Hg of vacuum, facilitating a flaccid penis to be re-inserted, or slid back fully within the device, as desired. Such manipulation may be repeated, stimulating the male organ, until the user reaches orgasm.

Figure 8:
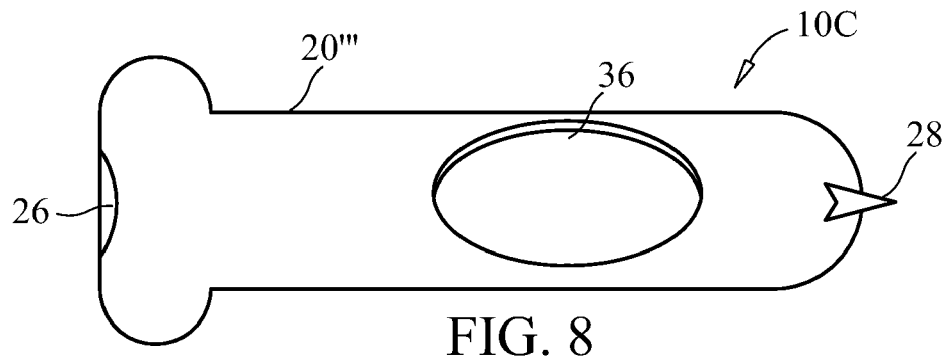
FIG. 8 is depicts a rigid enclosure of a further embodiment 10C of the masturbation device of the subject invention with an elliptical cutout disposed in the wall thereof.
Figure 9:
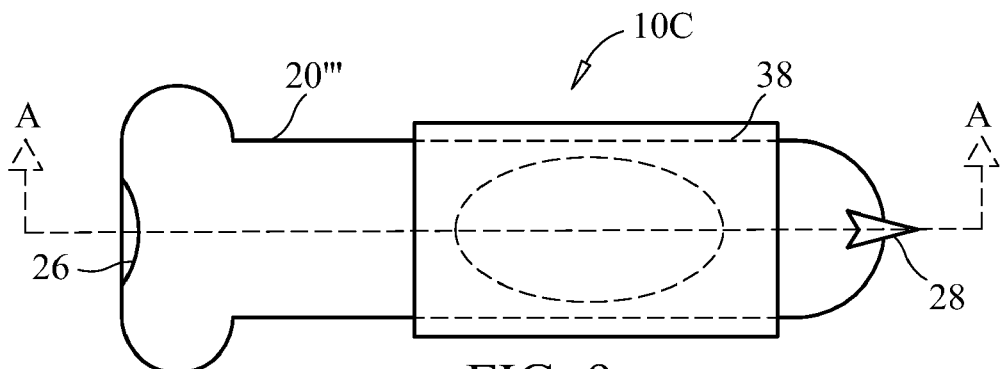
FIG. 9 illustrates a depressible tubular gripper encircling the rigid enclosure of device 10C shown in FIG. 8.
Figure 10:
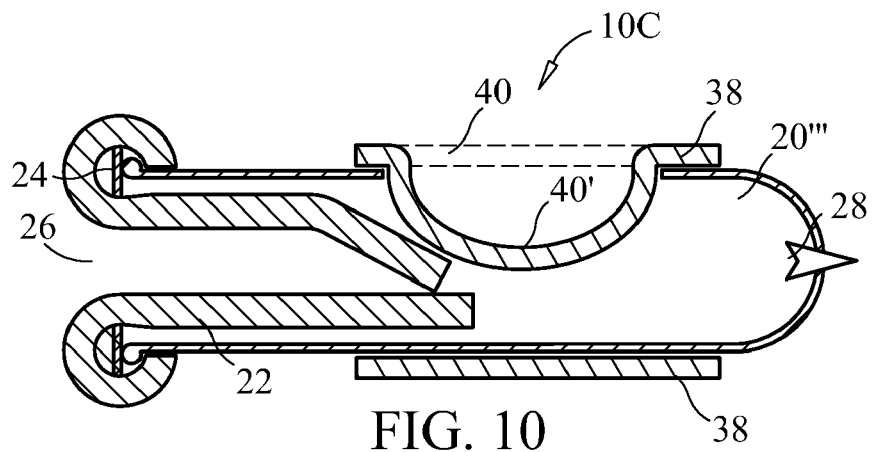
FIG. 10 schematically illustrates a cross-sectional side view, taken along line A-A of FIG. 9, illustrating the preferred embodiment masturbation device 10C of FIGS. 8 & 9, ready for use (with a flaccid penis) comprising an integrated accumulator means, variable aperture, resilient masturbation sleeve, and enclosure, showing the depressible tubular gripper having been manually depressed into the elliptical cutout in the enclosure (the user's hand or thumbs not shown, for clarity).

The foregoing description of the operational aspects of device 10A applies equally to the operation of device 10C depicted in FIGS. 8-10.

The design of enclosure 20' is not limited to that depicted in FIG. 6 wherein the depressible portion is located in the middle of the enclosure. Alternative enclosure designs are equally effective including, for example, an enclosure design wherein the proximal half of the enclosure is rigid, while the distal half of the enclosure is flexible.

Figure 6B:
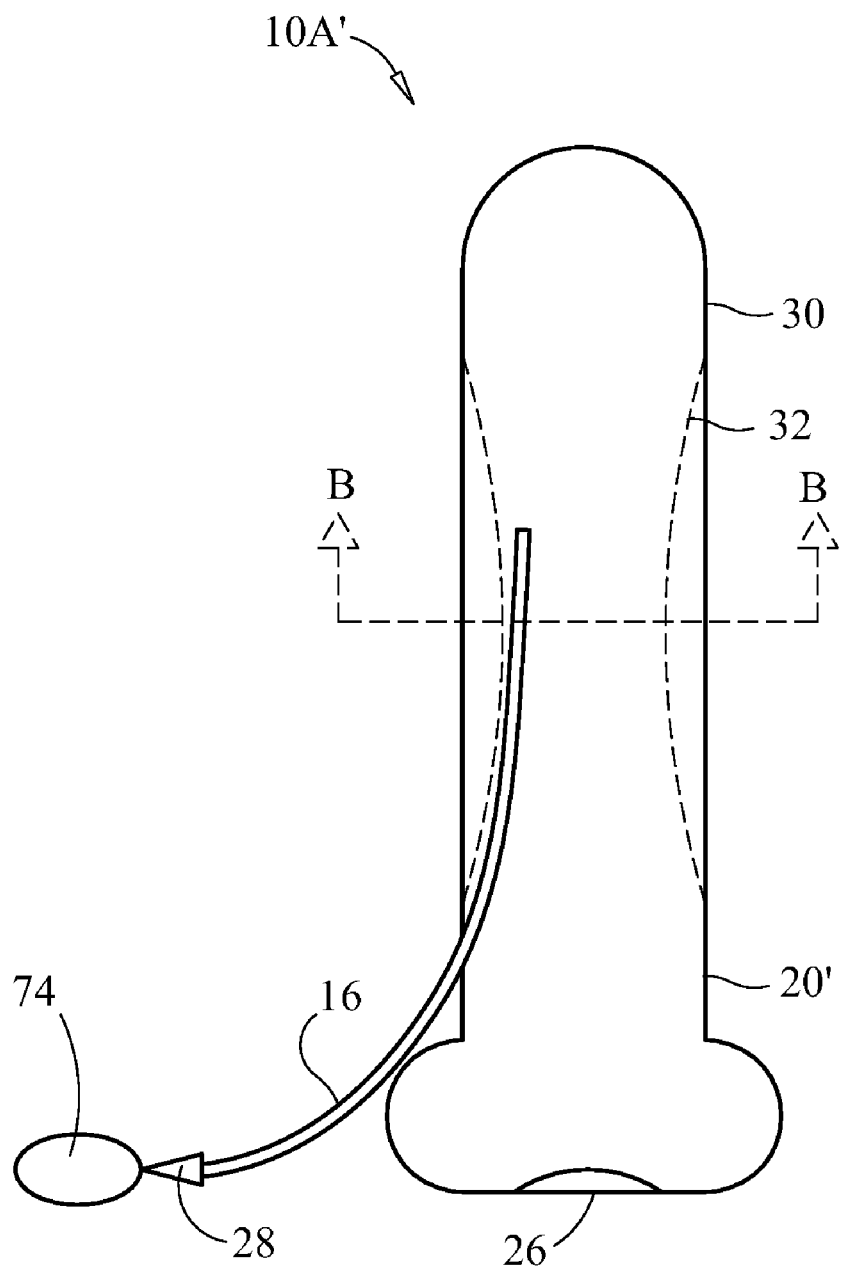
FIG. 6B schematically illustrates a further preferred embodiment 10A' of the masturbation device of the present invention which is adapted to be inserted into a bodily orifice of a partner.

FIG. 6B schematically illustrates a further preferred embodiment 10A' of the masturbation device of the present invention which is adapted to be inserted into a bodily orifice of a partner. Device 10A' is essentially a modified version of device 10A, such modifications being necessitated by the fact that the inserted portion of device 10A' will be inaccessible during use. The modifications are (1) check valve 28 has been relocated so that exhaust air will not be expelled into a body cavity and (2) initial insertion of a flaccid penis is effected by the momentary actuation of vacuum source 74 by either partner. Vacuum source 74 would not be needed during subsequent coitus-like stroking unless and until there occurred inadvertent air leakage past the aperture/penis hermetic seal at central opening 26, in which event vacuum source 74 would be momentarily employed, by either partner, to expel the unwanted air. With practice, most partners would learn to avoid such interruptions caused by air leakage.

In other respects, the accumulator means of insertable device 10A' is similar to that of device 10A, whereby the depressible enclosure 20' provides the accumulator means which enables use with a flaccid penis. Initial insertion of a flaccid penis into device 10A' may occur either before or after the device is inserted into a bodily orifice of a partner.

Figure 7:
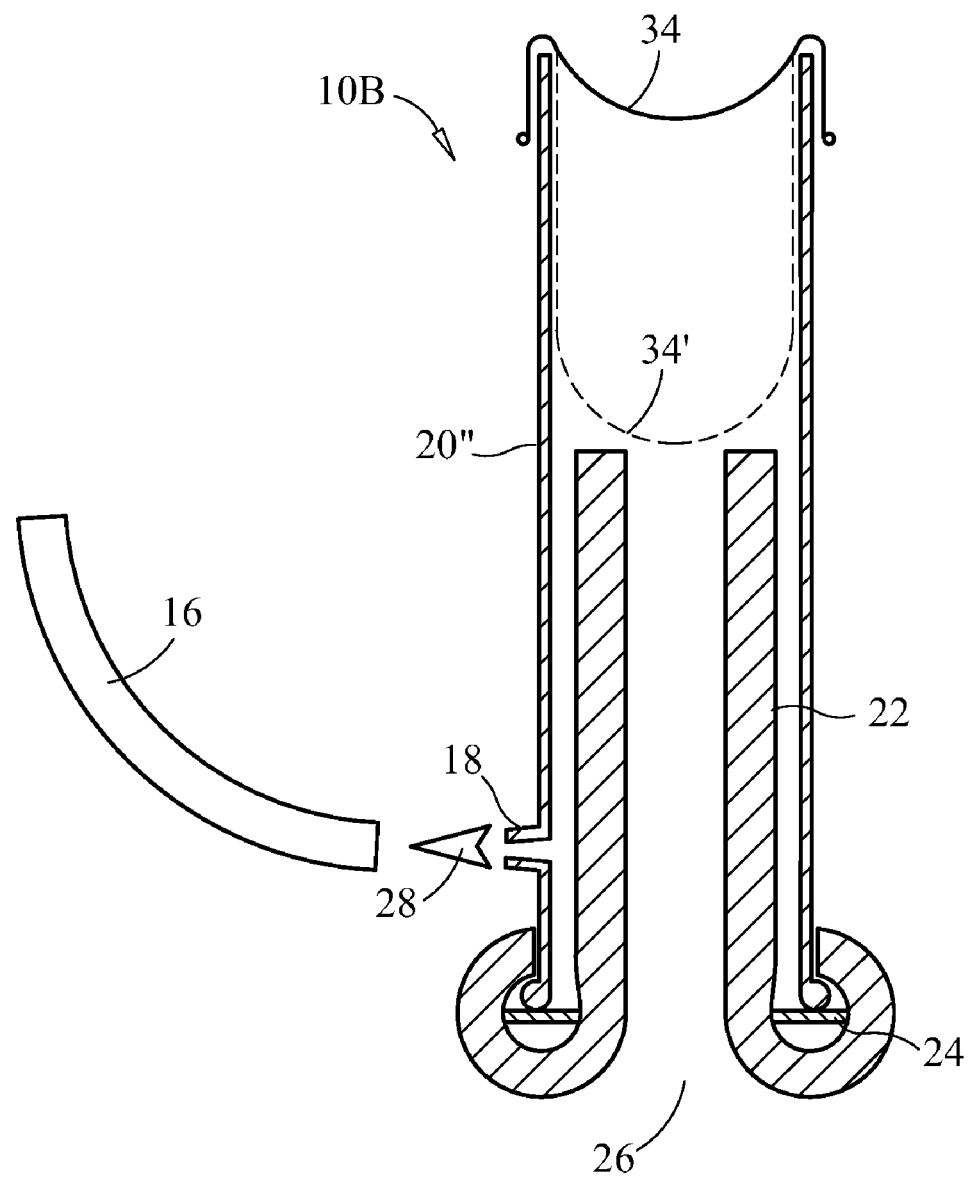
FIG. 7 schematically illustrates a longitudinal cross-sectional side view illustrating a further alternative masturbation device 10B wherein a flexible membrane disposed at the distal end of the housing together with a check valve functions in the manner of an integrated accumulator means.

FIG. 7 illustrates a further preferred embodiment 10B of the masturbation device of the present invention with an integrated accumulator and an optional charging means (not shown).

According to this embodiment, the distal end of alternative enclosure 20" is fitted with a flexible membrane 34. One end of optional flexible tube 16 is inserted over the exhaust end of check valve 28. The other end of the optional flexible tube 16 attaches to an optional remote vacuum source (not shown) such as a squeeze bulb, or other device.

With a lubricated glans penis sealing central opening 26, two alternative accumulator charging means become available to the user for causing a lubricated flaccid penis to be drawn into resilient masturbation sleeve 22. First, an optional remote vacuum source attached to tube 16 may be actuated (as for example squeezing and releasing a squeeze bulb) to draw air into tube 16 from enclosure 20" through check valve 28, thus creating a partial vacuum to draw the penis into sleeve 22. Alternatively, using fingers or other implement, flexible membrane 34 may be pressed inwards towards the proximal end of enclosure 20" such that it approximately assumes depressed state 34', causing air to be expelled through check valve 28 while opening 26 is blocked by a glans penis. Releasing the depressing force on flexible membrane 34 creates a modest vacuum within enclosure 20", causing the penis to be drawn into resilient masturbation sleeve 22. Partially withdrawing the penis causes flexible membrane 34 to stretch inward towards position 34', as a result of increased air volume and corresponding reduced air pressure within enclosure 20", facilitating easy re-insertion of a flaccid penis.

In the event of an inadvertent air admission at the proximal end of sleeve 22, the process described above may be repeated, using either or both of the remote or manual accumulator charging means, to expel unwanted air and to draw the penis fully within sleeve 22 such that the user may resume manipulating the penis back and forward within sleeve 22 facilitating masturbation, and orgasm.

A further preferred embodiment 10C of the masturbation device of the present invention is schematically shown in FIGS. 8-10. In this embodiment, a cutaway section 36 in the middle portion of enclosure 20''' is cut away as depicted in FIG. 8. A depressible tubular gripper 38 encircles the middle portion of enclosure 20''', hermetically sealing cutaway section 36 as depicted in FIG. 9. Check valve 28 is installed at a convenient location on enclosure 20'''. The combination of cutaway section 36, depressible tubular gripper 38 and check valve 28 comprises the integrated accumulator means of device 10C.

The operation of masturbation device 10C is similar to that of device 10A (FIG. 6) and device 10B (FIG. 7). While blocking central opening 26 with his lubricated glans penis, the user depresses that portion of depressible tubular gripper 38 covering cutaway section 36 with, for example, his thumbs. The surface of depressible tubular gripper 38 above cutaway section 36 is thereby deformed from a native state 40 to a depressed state 40' as shown in FIG. 10, which is a cross-sectional view taken along Line A-A of FIG. 9. This causes air to be expelled through check valve 28 and causes the penis to be drawn into resilient masturbation sleeve 22 through central opening 26 upon releasing the depressing force on depressible tubular gripper 38. The user may move device 10C forwards and backwards relative to the user, causing the penis to be stroked within sleeve 22. The increased vacuum created by moving device 10C away from the user, partially withdrawing the penis, causes depressible tubular gripper 38 to be drawn (sucked) into cutaway section 36. Re-insertion of the penis slightly reduces the vacuum pressure within device 10C thereby causing depressible tubular gripper 38 to lessen its incursion into cutaway section 36, in conformance with its function as an accumulator means. As should be readily apparent, these actions may stimulate the penis and facilitate masturbation and orgasm.

Figure 11:
FIG. 11 and FIG. 12 each illustrate alternate commercially available resilient masturbation sleeves which may be substituted for the tubular gripper depicted in FIGS. 9 and 10.
Figure 12:

FIGS. 11 and 12 depict examples of commercially available masturbation sleeves 42a and 42b which may be employed as depressible tubular gripper 38 to enhance the visual attractiveness of device 10C. Highly elastic, these sleeves 42a and 42b can grip a finger, yet easily stretch to slide onto an approximately 2.5 inch diameter cylinder such as enclosure 20''', and thus be integrated into device 10C. Acting as the accumulator means, portions (breasts, buttocks, for example) of sleeves 42a or 42b will move rhythmically up and down under the influence of changing vacuum pressure caused by stroking of the device, providing visual fantasy stimulation to the user.

Figure 13:
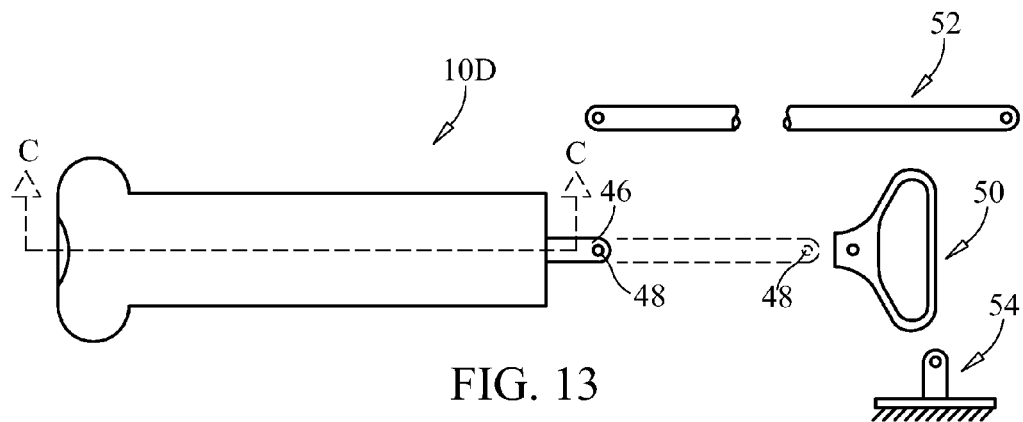
FIG. 13 is a schematic drawing of masturbation device embodiment 10D showing details of the integrated accumulator means employed in this embodiment.
Figure 14:
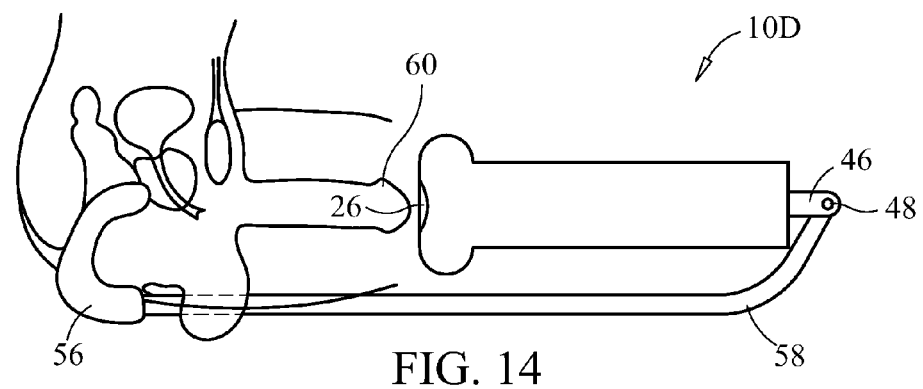
FIG. 14 is a schematic drawing of a prostate massage apparatus mechanically connected to and interacting in a reciprocal manner with the integrated accumulator means of device 10D.
Figure 15:
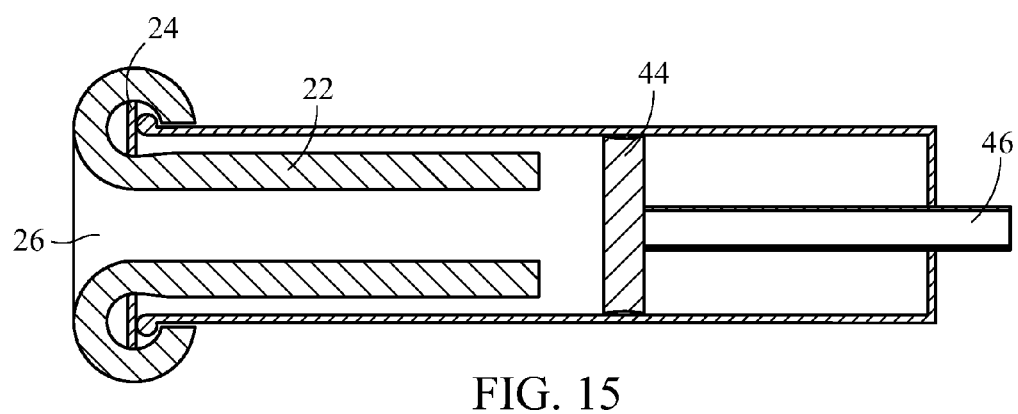
FIG. 15 is a schematic longitudinal cross-section taken along line C-C of FIG. 13 showing the housing and internal components of the masturbation device 10D.

Schematically depicted in FIGS. 13 through 15 is a further preferred embodiment 10D of the masturbation device of present invention that can be interconnected with a prostate massage apparatus 56 to provide the user with a prostate massage simultaneously with masturbation of a flaccid penis, whereby the user's stroking motions are transmitted directly to the prostate, as pressure pulses, at the same stroking frequency determined from time to time by the user.

Device 10D is similar to device 10B (illustrated in FIG. 7) except that a nipple and check valve are not required. Referring first to FIG. 15, a longitudinal cross section taken along line C-C of FIG. 13, the flexible membrane 34 of device 10B (FIG. 7) is replaced in device 10D with a piston 44 connected to a piston rod 46. Other components, for example, a diaphragm, could be substituted for piston 44. Piston rod 46 protrudes from an opening in the distal end of device 10D and is restrained, together with piston 44, from longitudinal movement relative to the user's body by one of at least the following three alternative methods.

First, the distal end of piston rod 46 may be fitted with an optional handle 50 (FIG. 13) to be held in one of the user's hands while the user uses his other hand to move the device in a stroking motion relative to the user's body. In this case the user may sit, stand, lie down, or move about while holding handle 50 and stroking device 10D.

Alternatively, an adjustable-length extension rod 52 (FIG. 13) may be attached through ball-joint connection pivot 48 to the distal end of piston rod 46, while the opposing end of extension rod 52 is connected in similar fashion to a stationary mount 54. Stationary mount 54 may be secured through any of a variety of conventional means (clamp, suction cup, Velcro, etc.) to a desk, bathroom fixture, or other household object located in front of the user. In this case the user will not move about while using the device, but may assume any desired bodily position. Alternatively, optional handle 50 may be attached at the distal end of adjustable-length extension rod 52 whereby it may be held by the user's foot, for example, or by a partner. As will be obvious to persons skilled in the art, some or all of the energy required to slide piston 44 may be provided by an external energy source and such modification should be deemed within the intent and scope of the instant invention.

Lastly, to use device 10D as a combined prostate massage/masturbation device, prostate massage extension rod 58 (which should be of adjustable length, to accommodate dimensional variability of users' anatomy) may be secured to a prostate massage apparatus 56 as illustrated in FIG. 14. Prostate massage apparatus 56, made of semi-resilient material such as rubber or silicone, when inserted into the user's anus, substantially restrains piston 44 from longitudinal movement relative to the user's body while transmitting cyclical piston forces directly to the user's prostate. The prostate-massage-apparatus 56/extension-rod 58 assembly illustrated in FIG. 14 may be pre-inserted and secured with a rubber-band-like silicone doughnut (not shown) that is placed around extension rod 58 and the user's testicles to secure prostate massage apparatus 56 in position on the user's body such that the user may move about, with prostate massage apparatus 56 inserted, even before connecting extension rod 58 to piston rod 46 at ball-joint connection pivot 48. During use, the user may sit, stand, lie down, or freely move about.

The manner of use of device 10D with a flaccid penis is as follows. With (1) the length of extension rod 58 suitably adjusted, (2) piston 44 bottomed out (touching or in near proximity to sleeve 22 as shown in FIG. 15) and (3) with piston rod 46 in some manner longitudinally restrained (relative to the user's body), the user merely places his lubricated glans 60 at central opening 26 of device 10D and pulls the device toward his body until the flaccid penis is fully inserted (all the way to the pubic bone, if desired). Because the diameter of piston 44 substantially exceeds the diameter of the penis, a flaccid penis will typically be pulled into the device a distance substantially exceeding the distance by which piston 44 was stroked, such excess volumetric capacity (piston displacement) being sufficient to compensate for lost motion inherent in this prostate-powered piston-accumulator arrangement.

The piston-accumulator of device 10D differs in several respects from the accumulators employed in masturbation device embodiments 10-10C which may be pre-charged (initial pressure established) prior to use and, absent air leakage, need not be re-charged during use. A piston accumulator like the one depicted in FIGS. 13-15, on the other hand, is not pre-charged at all, it need not store negative-pressure air between strokes, and is not negatively affected by air leakage (whether at central opening 26 or around the piston), because the accumulator has excess volumetric capacity and self-recharges with each stroke (there being no necessary carry-over of parameters of prior strokes).

Piston accumulators like the one depicted in FIGS. 13-15 have, as an additional differentiation from the other types of accumulators, the fact that the nonworking side of the piston (the piston rod side) produces an air flow to and from the device (respiration-like intake and exhaust, which may be directed to separate ports—not shown) with each stroke of the device. This cyclical air movement, while having no direct utility for the masturbation function of device 10D, nevertheless may be harnessed to power ancillary functions to erotically stimulate the user's visual, auditory, and olfactory senses, timed in synchronization with the stroking frequency selected from time to time by the user. For example, each insertion of the penis can actuate, in a rhythmic fashion, (1) movement of an erotic object (as with device 10C) or photograph flexibly affixed to the device, (2) sounds such as, for example, feminine squeals, and (3) odorant (perfume) dispersal. Also, a variable restriction (adjustable flow-control device) placed in the air inlet path (not shown) can serve to adjust the force placed against the prostate with each penis withdrawal on the outward stroke.

Thus the combined prostate massage/masturbation device 10D as depicted in FIG. 14 can produce simultaneous tactile stimulation of the prostate, sphincter, perineum, testicles, and penis tissues, even in the complete absence of an erection, while adding concurrent and coordinated erotic stimulation for the eyes, ears, and nose, capabilities which can extend the benefits of orgasm to many additional males.

Schematically depicted in FIGS. 16 and 16A is a further preferred embodiment 10E of the masturbation device of the present invention with an integral accumulator comprised principally of an inflatable element 62 (typically, a balloon) which is secured through the wall of device 10E by means of tapered breather tube 68, which may be constructed of rigid plastic. Prior to use, the accumulator of device 10E may be pre-charged by inflating inflatable element 62 to its inflated state 64. Inflation may be accomplished by supplying pressurized air to breather tube 68 by inserting therein the proximal end of resilient inflation tube 66, which encloses check valve 28, whereby inflatable element 62 will remain inflated (pre-charged) until resilient inflation tube 66 is removed from breather tube 68. Typically, just prior to use, the user will inflate (pre-charge) the accumulator orally by blowing air into resilient inflation tube 66, but may alternatively choose to employ non-oral inflation means such as, for example, a squeeze bulb (not shown).

To use device 10E, the user pre-charges its accumulator, places his lubricated glans to block central opening 26, and then removes inflation tube 66 from breather tube 68, whereby ambient atmospheric pressure allows partial deflation of inflatable element 62, thereby creating a modest vacuum of approximately 5 cm Hg within device 10E such that the flaccid penis is drawn fully into the device. As the user strokes the device, inflatable element 62 will automatically partially deflate with each insertion stroke, and will re-inflate with each withdrawal stroke, such that inflatable element 62 does not obstruct penis entry.

From time to time during use, the user may adjust the inflation volume of inflatable element 62 in order to either (1) increase or decrease the suction force, or (2) expel unwanted air which may have entered through central opening 26 during stroking. To decrease inflation and suction force, the user merely intentionally allows a limited amount of air to enter through central opening 26. To increase inflation and suction force during use, the user will cause some of the air contained within the device to be expelled through check valve 28 which is installed through the wall of the device near its distal end as shown in FIG. 16. Such expulsion of air is effected in the following manner. With the penis partially withdrawn from the device, the user merely places a finger over the opening of breather tube 68 and then vigorously pushes the device against his body, causing air to be expelled through the second check valve 28 which is installed through the wall of device 10E near its distal end. Said finger is then removed from the opening of breather tube 68 prior to a withdrawal stroke, during which increased inflation of inflatable element 62 will occur, resulting in an increased suction force being applied to the penis. Repeating this procedure (expelling additional air) will cause increased inflation and suction, until the penis and inflatable element 62 are jostling for space. With practice, a proficient user would learn to increase suction without missing a stroke, by quickly placing a finger over the opening of breather tube 68 during any regular inward stroke.

It is to be noted that the foregoing re-inflation procedure does not require use of resilient inflation tube 66, which had been previously removed and set aside. It is further noted that an experienced user might learn to refine his technique whereby he can use the foregoing procedure to cause the initial inflation, without employing a pressurized air supply (oral or otherwise) and thus without using inflation tube 66.

The function of internal rib 70 is to provide an air path 72 such that all contained air has an escape path, past inflatable element 62, as shown in FIG. 16A, and through check valve 28 which is installed in the wall of device 10E near its distal end.

Figures 17, 17A:
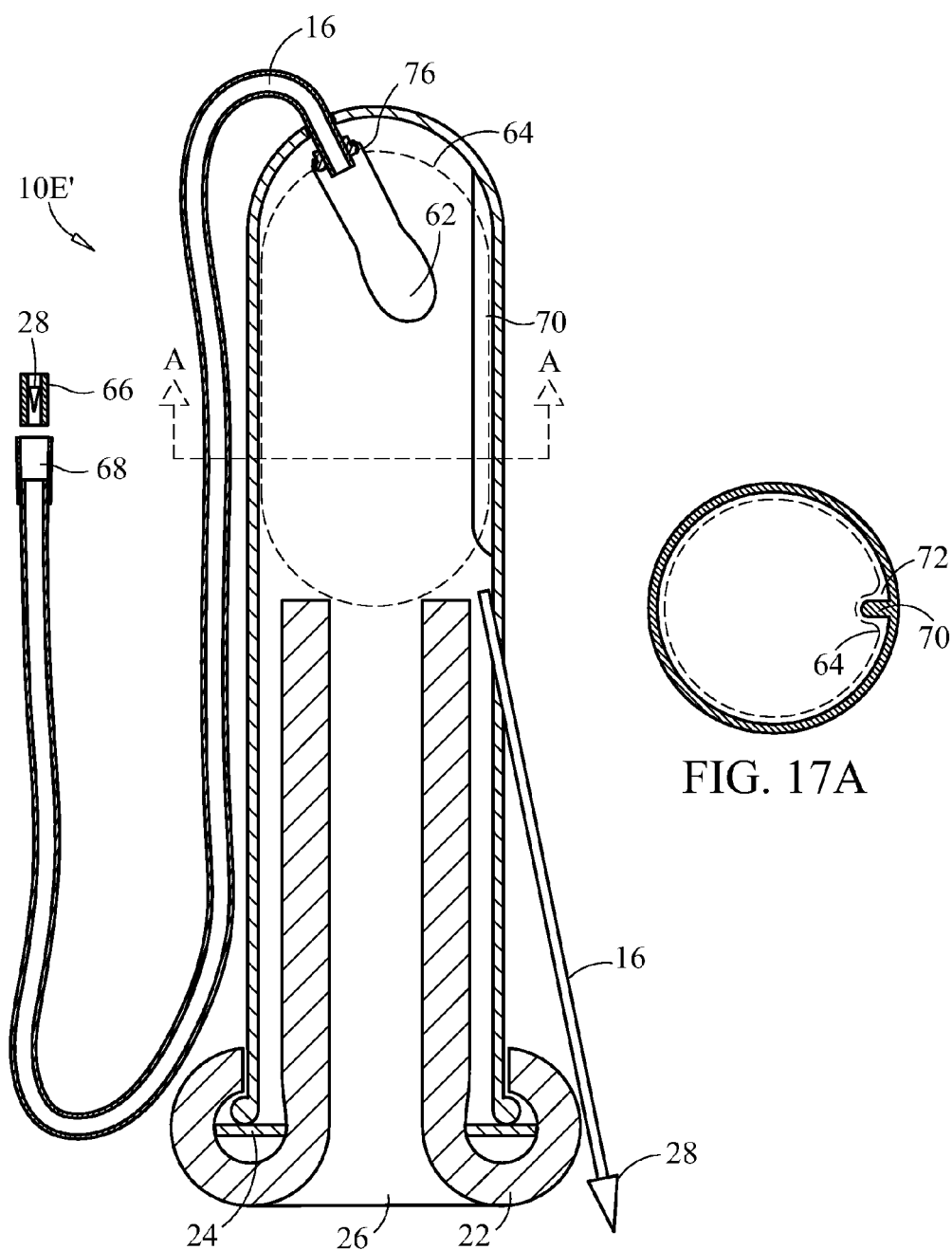
FIG. 17 schematically illustrates masturbation device embodiment 10E' comprising modifications to device 10E such that a portion of the device may be inserted into a bodily orifice of a partner.
FIG. 17A is a cross-sectional view taken along line A-A of FIG. 17.

Schematically depicted in FIGS. 17 and 17A is a further preferred embodiment 10E' of the masturbation device of the present invention which is operationally similar to device 10E, but which includes modifications enabling a portion of device 10E' to be inserted into a bodily orifice of a partner during use. Such modifications comprise (1) relocating a check valve 28 such that exhaust air is not expelled into a body cavity and (2) providing inflation means which is accessible while a portion of the device is inserted. While the relocated check valve 28 is schematically depicted in FIG. 17 as being disposed at the end of a length of flexible tube 16, the air path provided by said flexible tube 16 may alternatively be provided, for example, by being molded integrally with the exterior wall of the device.

Inflatable element 62 is secured to breather nozzle 76 which is in turn connected to flexible tube 16 which extends outside the partner's body where it is connected to breather tube 68 into which resilient inflation tube 66 may be inserted. As with device 10A', initial insertion of a flaccid penis into device 10E' may occur either before or after a portion of the device is inserted into a bodily orifice of a partner.

The method of use of device 10E', including initial inflation of inflatable element 62, and subsequent adjustment of inflation and suction, is as described above with respect to device 10E, except that stroking is accomplished by coitus-like movement by the user and partner, and either partner may increase inflation and suction during use.

SUMMARY AND SCOPE

As will be appreciated, the masturbation device of the present invention provides a simple, inexpensive, safe and comfortable means to promote masturbation, orgasm and ejaculation in males without requiring the subject to achieve a partial or full erection. The device is useful and therapeutic to those suffering ED as well as those who may wish to engage in masturbation, or to collect semen, without concern whether their penis achieves an erection. Furthermore, even in the absence of ED, the user may start masturbating immediately, before his erection occurs, thus reducing the time required to reach orgasm.

The device employs conventional components in a novel and innovative manner to maintain a modest vacuum that both secures a flaccid penis within the device and maintains the penis there during manipulations facilitating orgasm. It offers an inexpensive and safe alternative to pharmaceuticals and mechanical vacuum devices designed to produce an erection, but not orgasm.

Although the invention has been described with reference to specific embodiments, structures, configurations and methods, this description is not meant to be construed in a limiting sense. Various modifications of the disclosed embodiments, as well as alternative embodiments of the invention, will become apparent to persons skilled in the art upon reference to the description of the invention.

By way of example, diaphragms, bellows and other means for controlling fluids may be substituted for the accumulator components described with respect to the preferred embodiments without departing from the spirit and scope of the taught invention. Means other than those shown and described can be used to maintain the modest vacuum within the masturbation device. A variety of accessories such as, for example, visuals, photos, audio, video, motion, touch, taste, odorants, makeup, heat, vibration, lubrication system, resilient masturbation sleeve, external energy source, remote control, wireless remote, mounts, male condom, female condom, scrotum retractor, concealment, disguise, container, prostate probe, perineum probe, exerciser, wearable accessories, female/couple accessories familiar to those of ordinary skill in the art, may be employed with the device. The device may be formed and shaped to simulate human features that are likely to please and arouse the user. All such modifications should be deemed within the intent and scope of the instant invention.

The invention claimed is:

1. A device for facilitating male orgasm with a flaccid penis comprising
   a. a housing having an opening to receive a penis;
   b. an accumulator means functioning to maintain within said housing a partial vacuum at a pressure which is not less than 0.8 bar absolute pressure notwithstanding movement of the penis within said housing;
   whereby the benefits of orgasm may be imparted to a user with erectile dysfunction without resort to drugs or vacuum erection devices.

2. The device of claim 1 wherein said accumulator means is integrated with said housing.

3. The device of claim 1 wherein a portion of said housing is resilient and depressible to comprise component of said accumulator means.

4. The device of claim 1 wherein said accumulator means is not integrated with said housing but is in fluid communication therewith.

5. The device of claim 1 wherein said accumulator means includes one or more components selected from the group comprising a bellows, spring, piston, cylinder, valve, balloon, check valve, squeezable bulb, pump, squeezable cylinder, inflatable element, and diaphragm.

6. The device of claim 1 wherein said partial vacuum is created orally by blowing or sucking into said accumulator means or housing.

7. The device of claim 1 wherein said partial vacuum is maintained within the range of 4 cm Hg to 7 cm Hg.

8. The device of claim 1 wherein the partial vacuum is maintained within the range of 0.5 cm Hg to 15 cm Hg.

9. The device of claim 1 further comprising a variable aperture means disposed at the opening of said housing functioning to create a hermetic seal around a lubricated penis.

10. The device of claim 9 wherein said variable aperture means functions to maintain a hermetic seal around said lubricated penis while the diameter of said penis expands and contracts.

11. The device of claim 1 further comprising a prostate massage means.

12. The device of claim 11 wherein said prostate massage means comprises an elongate member in mechanical communication with said housing such that manipulation of the housing serves to manipulate said prostate massage means.

13. The device of claim 1 further comprising one or more sensory stimulation means functioning to enhance the experience of the user or two persons using the device together.

14. The device of claim 13 wherein said sensory stimulation means are selected from a group comprising photos, physical objects depicting human forms, audio recordings, sound generator, video recordings, odorants, taste-able substance, makeup, heat, vibration including operated remotely, harness, resilient sleeve, lubrication system, mounts, male condom, female condom, scrotum retractor, prostate probe, perineum probe, concealment, disguise, exerciser, wearable accessories, female/couple accessories.

15. The device of claim 1 wherein said housing is substantially restrained such that sliding of the penis within said housing may be effected by movement of the user's body.

16. The device of claim 1 wherein a portion of said housing is adapted to be inserted into a bodily orifice whereby the device may be used with a partner.

17. An apparatus for facilitating male orgasm with a flaccid penis comprising a housing having an opening to receive a penis and an inflatable element functioning to maintain within said housing a partial vacuum at a pressure which is not less than 0.8 bar absolute pressure notwithstanding movement of said penis within said housing.

18. A method for facilitating male orgasm with a flaccid penis comprising
   a. providing a device comprising a housing having an opening to receive a penis and an accumulator means functioning to maintain within said housing a partial vacuum at a pressure which is not less than 0.8 bar absolute pressure notwithstanding movement of the penis within said housing;
   b. placing the glans of a lubricated penis at the opening of said housing;
   c. actuating said accumulator means to draw said glans into said housing;
   d. sliding said glans within said housing, or sliding said housing relative to said glans, to stimulate said glans and facilitate orgasm.

19. The method of claim 18 wherein said housing is substantially restrained such that moving the user's body relative to said housing effects sliding of said glans within said housing.

20. The method of claim 19, wherein said housing is substantially restrained by insertion of a portion of said housing into a bodily orifice of a partner.

21. The method of claim 19, wherein said housing is restrained by anchoring said housing to a relatively stationary object.

22. The method of claim 18 wherein said accumulator means provided is integrated with said housing.

23. The method of claim 18 wherein a portion of said housing provided is resilient and depressible to comprise component of said accumulator means.

24. The method of claim 18 wherein said accumulator means provided is not integrated with said housing but is in fluid communication therewith.

25. The method of claim 18 wherein said accumulator means includes one or more components selected from the group comprising a bellows, siphon, spring, piston, cylinder, valve, balloon, check valve, squeezable bulb, pump, squeezable cylinder, inflatable element, and diaphragm.

26. The method of claim 18 wherein said partial vacuum is maintained within the range of 4 cm Hg to 7 cm Hg.

27. The method of claim 18 wherein the partial vacuum is maintained within the range of 0.5 cm Hg to 15 cm Hg.

28. The method of claim 18 wherein said device further comprises a variable aperture means disposed at the opening of said housing functioning to create a hermetic seal around said lubricated penis.

29. The method of claim 28 wherein said variable aperture means functions to maintain a hermetic seal around said lubricated penis while the diameter of said penis expands and contracts.

\* \* \* \* \*

UNITED STATES PATENT AND TRADEMARK OFFICE
CERTIFICATE OF CORRECTION

PATENT NO. : 8,382,656 B1
APPLICATION NO. : 13/493374
DATED : February 26, 2013
INVENTOR(S) : Ronald Allen Brown It is certified that error appears in the above-identified patent and that said Letters Patent is hereby corrected as shown below:

In the Claims:

Column 16, claim 3, line 38, before the word "component" insert the word --a--.

Column 18, claim 23, line 15, before the word "component" insert the word --a--.

Signed and Sealed this
Sixteenth Day of April, 2013

Teresa Stanek Rea
*Acting Director of the United States Patent and Trademark Office*